United States Patent
Piemonti et al.

(10) Patent No.: US 9,556,115 B2
(45) Date of Patent: *Jan. 31, 2017

(54) SULFONAMIDES FOR THE PREVENTION OF DIABETES

(71) Applicant: Dompé S.P.A., L'Aquila (IT)

(72) Inventors: Lorenzo Piemonti, Milan (IT); Luisa Daffonchio, L'Aquila (IT); Marcello Allegretti, L'Aquila (IT)

(73) Assignee: DOMPÉ FARMACEUTICI S.P.A., Milan (MI) (IT)

( * ) Notice: Subject to any disclaimer, the term of this patent is extended or adjusted under 35 U.S.C. 154(b) by 294 days.

This patent is subject to a terminal disclaimer.

(21) Appl. No.: 14/497,637

(22) Filed: Sep. 26, 2014

(65) Prior Publication Data

US 2015/0011639 A1    Jan. 8, 2015

Related U.S. Application Data

(63) Continuation of application No. 13/500,522, filed as application No. PCT/EP2010/064920 on Oct. 6, 2010, now Pat. No. 8,846,755.

(30) Foreign Application Priority Data

Oct. 6, 2009 (EP) .................................. 09172365

(51) Int. Cl.
| | | |
|---|---|---|
| *A01N 41/02* | (2006.01) | |
| *A61K 31/255* | (2006.01) | |
| *C07C 311/51* | (2006.01) | |
| *A61K 31/185* | (2006.01) | |

(52) U.S. Cl.
CPC ........... *C07C 311/51* (2013.01); *A61K 31/185* (2013.01)

(58) Field of Classification Search
None
See application file for complete search history.

(56) References Cited

U.S. PATENT DOCUMENTS

| | | |
|---|---|---|
| 2003/0216392 A1 | 11/2003 | Bertini et al. |
| 2004/0242498 A1 | 12/2004 | Collins et al. |
| 2012/0202884 A1 | 8/2012 | Piemonti et al. |
| 2013/0059908 A1 | 3/2013 | Piemonti et al. |

FOREIGN PATENT DOCUMENTS

| | | |
|---|---|---|
| EP | 1123276 B1 | 1/2003 |
| EP | 1355641 B1 | 9/2005 |
| EP | 1776336 B1 | 9/2009 |
| EP | 2308485 A1 | 4/2011 |
| WO | WO02062330 A3 | 4/2003 |
| WO | WO2009117710 A3 | 1/2010 |
| WO | WO2011042465 A1 | 4/2011 |

OTHER PUBLICATIONS

Wasserfall et al., "Autoantibody markers for the diagnosis and prediction of type 1 diabetes," Autoimmunity Reviews, 2006, 5(6):424-428.
Aribi, "Candidate Genes Implicated in Type 1 Diabetes Susceptibility," Current Diabetes Reviews, 2008, 4:110-121.
Bakshi et al., Novel Role of CXCR2 in Regulation of gamma-Secretase Activity, ACS Chemical Biology, 3 (12):777-789, 2009.
Chavey et al., CXC Ligand 5 Is an Adipose-Tissue Derived Factor that Links Obesity to Insulin Resistance, Cell Metabolism, 9:339-349, 2009.
Buchanan et al., Preservation of Pancreatic Beta-Cell Function and Prevention of Type 2 Diabetes by Pharmacological Treatment of Insulin Resistance in High-Risk Hispanic Women, Diabetes, 51:2796-2803, 2002.
Gorio et al., Reparixin, an Inhibitor of CXCR2 Function, Attenuates Inflammatory Responses and Promotes Recovery of Function after Traumatic Lesion to the Spinal Cord, The Journal of Pharmacology and Experimental Therapeutics, 322(3):973-981, 2007.
Allegretti et al., Allosteric inhibitors of chemoattractant receptors: opportunities and pitfalls, Trends in Pharmacological Sciences, 29(6):280-286, 2008.
EPO Authorized Officer Jenny Olausson, PCT International Search Report and Written Opinion for International Application No. PCTIEP20101064920, mailed Nov. 18, 2010,13 pages.

*Primary Examiner* — Jeffrey S Lundgren
*Assistant Examiner* — Tori M Strong
(74) *Attorney, Agent, or Firm* — Fish & Richardson P.C.

(57) ABSTRACT

The use of sulfonamides of formula (I)

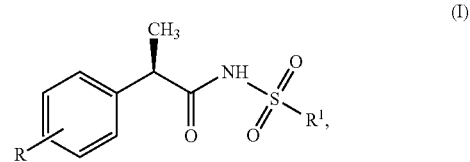

wherein R and $R^1$ are as defined in the description, for the preparation of medicaments for the prevention of diabetes, in particular of type-1 diabetes is herein disclosed.

17 Claims, 4 Drawing Sheets

SULFONAMIDES FOR THE PREVENTION OF DIABETES

CROSS-REFERENCE TO RELATED APPLICATIONS

This application is a continuation of U.S. patent application Ser. No. 13/500,522, entitled "Sulfonamides For The Prevention Of Diabetes" and filed on Apr. 5, 2012, which is a §371 National Stage Application of International Application Number PCT/EP2010/064920, entitled "Sulfonamides for the Prevention of Diabetes" and filed on Oct. 6, 2010, which claims priority to EP 09172365.0, entitled "Sulfonamides for the Prevention of Diabetes" and filed on Oct. 6, 2009, the entire contents of all of which are hereby incorporated by reference.

FIELD OF THE INVENTION

The present invention relates to the prevention of diabetes.

BACKGROUND OF THE INVENTION

Diabetes is a disease in which the body does not produce enough or is unable to respond to insulin, a hormone secreted by the pancreatic β-cells (Langerhans islet cells) that turns glucose into energy.

In greater detail, diabetes distinguishes into Type 1 diabetes, in which Langerhans islet cells do not produce insulin and which is in most cases of autoimmune origin, and Type 2 diabetes, a condition due to a defective responsiveness of the cells to insulin, usually combined with a reduced insulin secretion.

The therapy of Type 1 diabetes consists in the administration of artificial insulin via subcutaneous injections combined with a careful monitoring of blood glucose levels. The therapy of Type 2 diabetes in its initial stages consists in the administration of oral medicaments that improve insulin resistance, decrease glucose release by the liver and stimulate the increase of insulin secretion, but at later stages it requires also insulin administration.

Since both Type 1 and Type 2 diabetes are at least partially inherited, subjects with relatives suffering from this pathology have a certain risk of developing diabetes.

Furthermore, a series of predictive markers have been identified that are able to foretell the onset of diabetes, in particular Type 1 diabetes (Curr Diabetes Rev, 208, May 4(2), 110-121; Autoimmune Rev 2006 July, 5(6), 424-428). It is therefore possible to identify at low cost and with easy procedures individuals with high risk of developing the disease.

A number of attempts to control and/or delay the onset of diabetes in individuals at risk have been made; however, these require the use of therapies with too a high costs/benefits ratio. Therefore, at present, in spite of the availability of tools able to predict this disease, there is no adequate pharmacological treatment able to prevent or at least delay its onset.

The only strategy that can be adopted in subjects at risk is periodic monitoring of glycaemia and a healthy lifestyle, including control of body weight, physical exercise and adequate dietary regimen. However, this has a very limited efficacy.

Thus, there is a long felt need for medicaments for the prevention of diabetes.

EP 1 123 276 discloses N-(2-aryl-propionyl)-sulfonamides, among them R(-)-2-[(4-isobutylphenyl)propionyl]-methanesulfonamide (I), and their pharmaceutically acceptable salts, for use as inhibitors of neutrophil chemotaxis and degranulation induced by IL-8, in particular for use in the treatment of pathologies like psoriasis, rheumatoid arthritis, ulcerative colitis, acute respiratory insufficiency (ARDS), idiopathic fibrosis and glomerulonephritis.

EP 1 355 641 discloses the use of R(-)-2-[(4-isobutylphenyl)propionyl]-methanesulfonamide and pharmaceutically acceptable salts thereof, in particular its lysine salt, in the prevention and treatment of ischemia/reperfusion injury of transplanted organs and of functional injury resulting from rejection reactions after solid organ transplantation, in particular kidneys, which need to be retrieved from a donor and stored before transplantation. Such injuries are deemed to be responsible for delayed graft function, which makes dialysis necessary in case of renal transplantation.

EP 1 579 859 discloses the use of N-(2-aryl-propionyl) sulfonamides, among them R(-)-2-[(4-isobutylphenyl)propionyl]methanesulfonamide and its lysine salt, for the preparation of medicaments for the treatment of spinal cord injury.

DETAILED DESCRIPTION OF THE INVENTION

Figure 1:
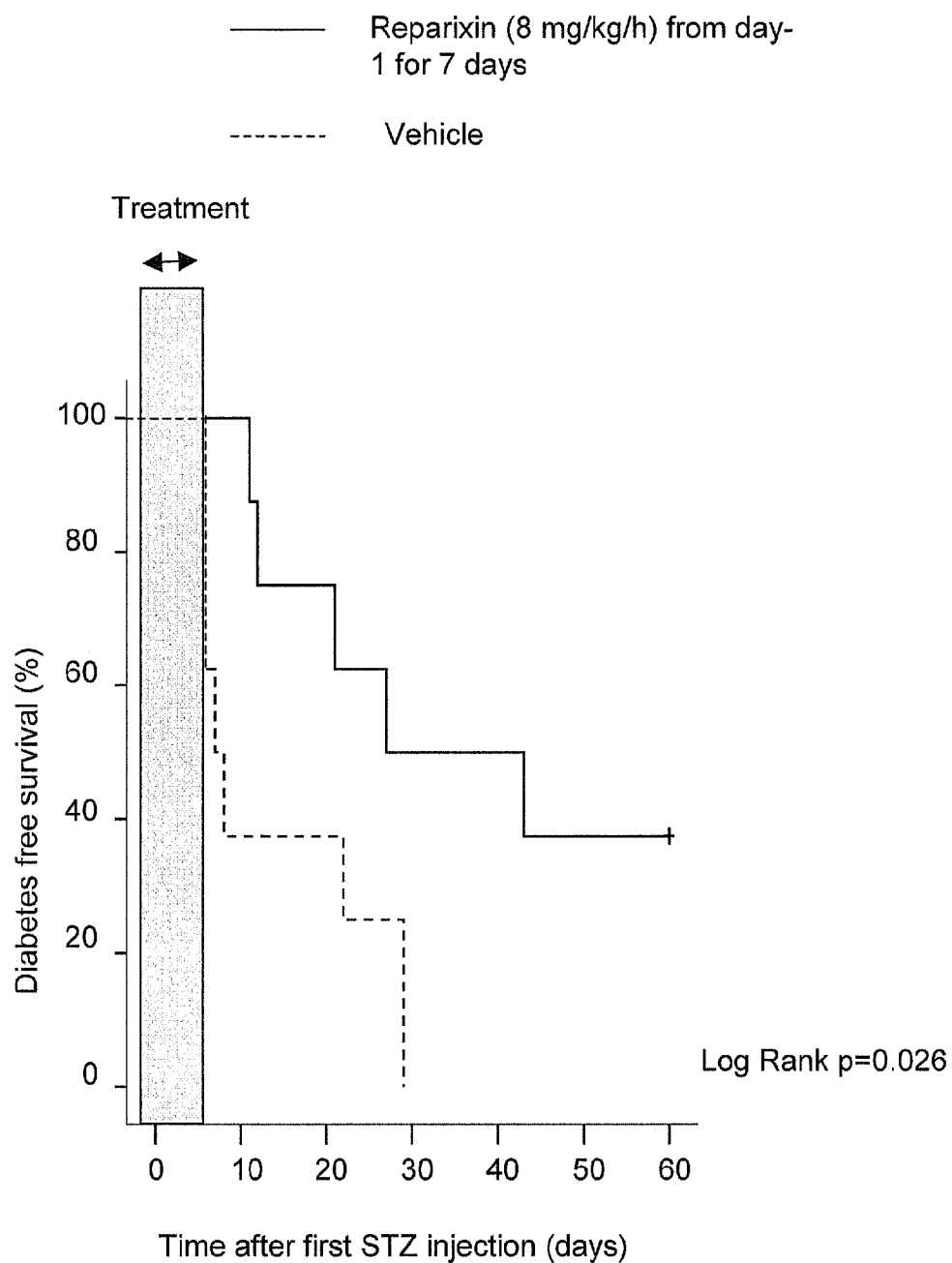
FIG. 1 shows the diabetes-free survival percentage over time (days) in mice treated with (ML)-streptozotocin (STZ) at day 0 for 5 days, following administration from day-1 of Vehicle (dotted line) or Reparixin (solid line) for 7 days.

It has now been found that compounds of formula I, or pharmaceutically acceptable salts thereof:

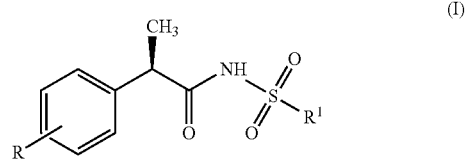

(I)

wherein R is selected from linear or branched 4-($C_1$-$C_6$) alkyl, 4-trifluoromethanesulfonyloxy and 3-benzoyl and $R^1$ is linear or branched ($C_1$-$C_6$)alkyl are able to protect pancreatic β-cells from structural and/or functional damage and to significantly delay the onset of diabetes as well as to reduce the severity of the disease, once this develops.

Particularly preferred compounds according to the invention are R(-)-2-[(4-isobutylphenyl)propionyl]-methanesulfonamide (commonly known as Repertaxin or Reparixin, hereinafter referred to as Reparixin) and R(-)-2-[(4'-trifluoromethanesulfonyloxy)phenyl]propionyl-methanesulfonamide (commonly known and hereinafter referred to as Meraxin).

Preferred salts of the compounds of the invention are the sodium and the lysine salt. Particularly preferred salts of the compounds of the invention are the lysine salt of Reparixin and the sodium salt of Meraxin.

As it will be described in the Experimental Section, mice injected with STZ, a compound able to induce a condition with clinical and histoimmunological features of human Type 1 diabetes, develop the disease in more than double the time in the presence of a treatment with Reparixin or Meraxin compared to controls. More importantly, in mice treated with Reparixin or Meraxin, even after development of diabetes, glycemic levels remain significantly lower than in control mice. These results clearly demonstrate that Reparixin and Meraxin are able to protect β-cells from injuries.

Thus, a first object of the present application is the use of the compounds of formula I or pharmaceutically acceptable salts thereof, preferably the lysine or sodium salts, for the preparation of a medicament for the protection of pancreatic β-cells from structural and/or functional injury.

Preferably, the compound of formula I is Reparixin or Meraxin.

A further object of the invention is the use of the compounds of formula I, preferably Reparixin or Meraxin, for the prevention of diabetes, preferably of Type 1 diabetes. The medicament is preferably administered to individuals having a predisposition to diabetes or starting to show the very first symptoms of diabetes.

In particular, this application relates to the use of the compounds of the invention, preferably Reparixin or Meraxin, for the manufacture of a medicament for delaying the onset and/or reducing the progression of diabetes, preferably of Type 1 diabetes.

The compounds of formula I can be prepared with procedures well known in the art. For example, Reparixin can be prepared as disclosed in Example 1 of EP 1 123 276 and in Example 1 of EP 1 355 641, while the lysine salt can be prepared as disclosed in Example 7 and Example 2, respectively, of the aforementioned patents. Meraxin can be prepared, for example, according to Example 1 of EP 1776336.

For the purposes of the present invention, the above compounds are formulated in pharmaceutical compositions suitable for use by oral administration, such as tablets, capsules, syrups, preferably in the form of controlled release formulations, or by parenteral administration, preferably in the form of sterile solutions suitable for intravenous or intramuscular administration. The pharmaceutical compositions can be prepared according to conventional methods, for example as disclosed in Remington, "The Science and Practice of Pharmacy", $21^{st}$ ed. (Lippincott Williams and Wilkins). Preferably, the amount of Reparixin or its pharmaceutically acceptable salt in each of the above-mentioned administration forms will be such as to provide between 2 and 15 mg compound or salt/kg body weight, while the amount of Meraxin or its pharmaceutically acceptable salt will be such as to provide between 10 and 20 mg compound or salt/kg body weight. In any case, the regimen and amount of medicament to be administered will be determined by the physician according to the patient's need.

The invention will be now further illustrated in greater detail in the following experimental section.

EXPERIMENTAL SECTION

Effect of Reparixin on Diabetes Induction After Multiple Low Dose (MLD)-Streptozotocin (STZ) Injections.

Injection of susceptible mice strains with multiple low doses of (STZ) provokes a condition with clinical and histoimmunological features similar to human Type 1 diabetes mellitus (DM). It has been established that five daily doses of 40 mg/kg/day of STZ are required for delayed onset, sustained and progressive hyperglycemia and insulitis in male C57BL/6 mice.

This model was previously used to study the role of proinflammatory cytokines in the development of Type 1 diabetes. 12 male C57BL/6J mice received MLD-STZ treatment. STZ was injected i.p. at a dose of 40 mg/kg/day, for 5 consecutive days. Glucose concentrations in venous blood was measured every day starting from the first day of treatment. Mice with glycemia over 250 mg/dl on three consecutive tests were considered diabetic, with the first detection of hyperglycemia taken as the date of diabetes onset. The mice were monitored for up to 60 days post first STZ injection. Reparixin was administered by s.c. continuous infusion starting from day −1 up to day 7 after first STZ injection at a dose of 8 mg/h/kg.

Figure 2:
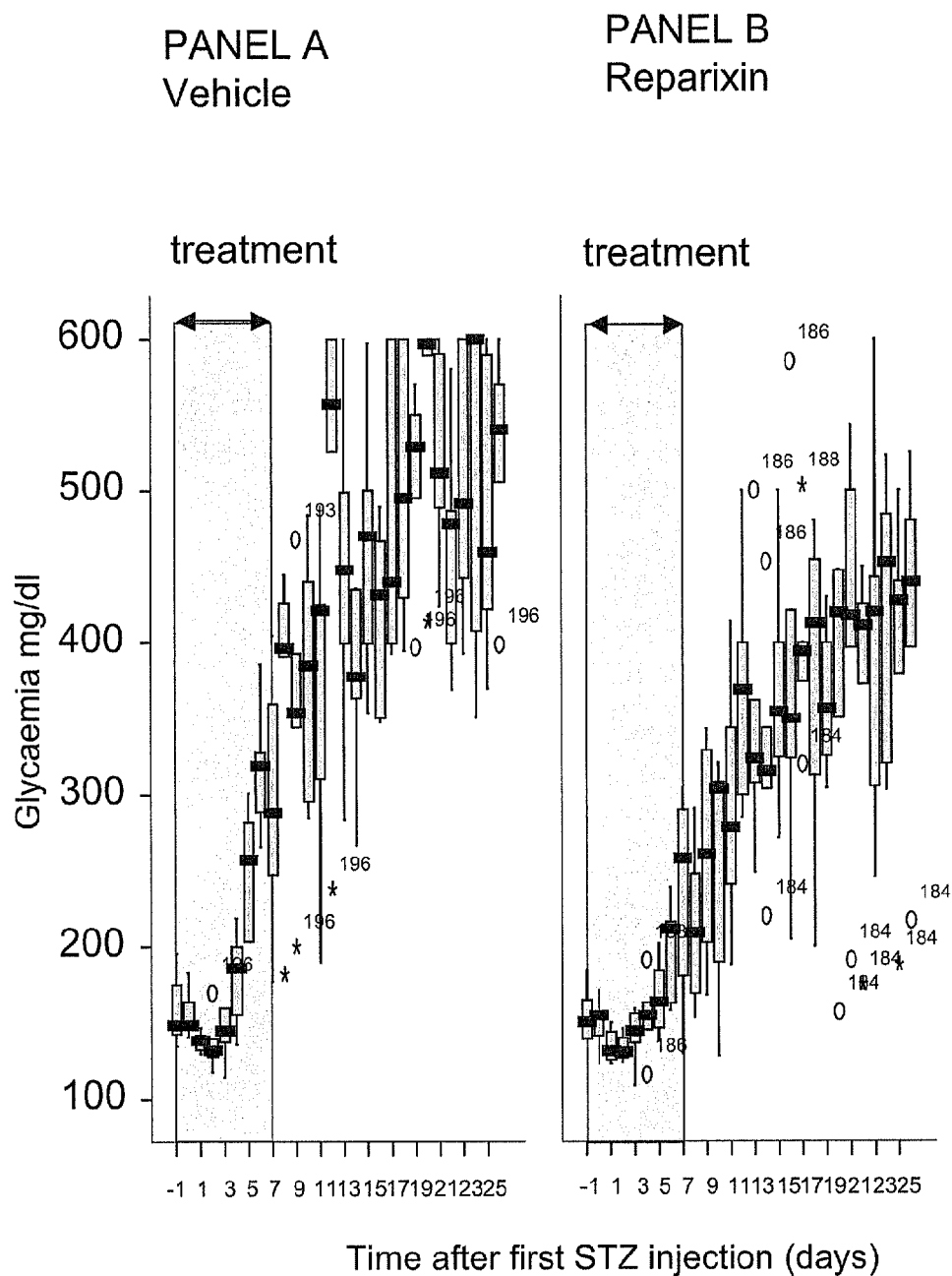
FIG. 2 shows the glycemia levels (mg/dl) over time (days) in mice treated with (ML)-streptozotocin (STZ) at day 0 for 5 days, following administration from day −1 of Vehicle (Panel A) or Reparixin (Panel B) for 7 days.

The administration of Reparixin significantly influenced the timing of diabetes development. The median diabetes free time was 27±15 days (n=8, p=0.026vs ctrl) and 7±0.5 days (n=8) respectively for Reparixin- and vehicle-treated mice (FIG. 1). More importantly, even after diabetes development, for the whole two-month observation period, glycaemia levels remained constantly and significantly lower in the Reparixin-treated group than in the vehicle-treated group (FIG. 2).

Effect of Meraxin on Diabetes Induction After Multiple Low Dose (MLD)-Streptozotocin (STZ) Injections.

Male C57BL/6J mice were injected i.p. with (ML)-streptozotocin (STZ) at a dose of 40 mg/kg/day, for 5 consecutive days. Glucose concentrations in venous blood were measured every day starting from the first day of treatment (day 0). Mice with glycaemia over 250 mg/dl on three consecutive tests were considered diabetic, with the first detection of hyperglycemia taken as the date of diabetes onset. The mice were followed for up to 60 days post first STZ injection. Meraxin was administered per os at a dose of 15 mg/kg for 7 or 14 days, starting from day −1 of first STZ injection.

Figure 3:
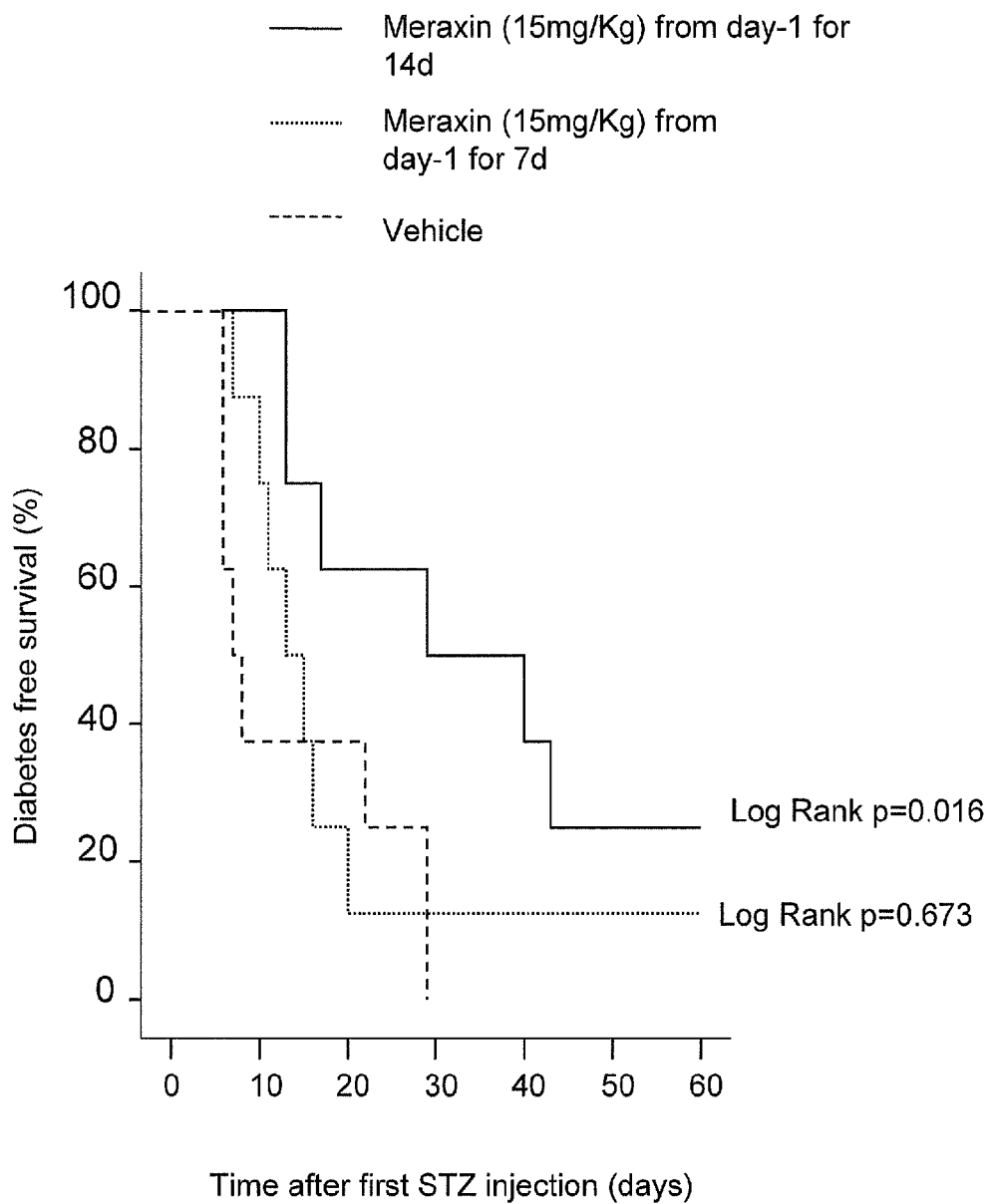
FIG. 3 shows the diabetes-free survival percentage over time (days) in mice treated with (ML)-streptozotocin (STZ) at day 0 for 5 days, following administration from day −1 of Vehicle, Meraxin (15 mg/Kg) for 7 days or Meraxin (15 mg/Kg) for 14 days.

In both cases, the treatment with Meraxin was able to prolong the diabetes-free time compared with control. The median diabetes-free time was 13+2.8 days (p=0.67 vs ctrl, n=8) and 29+16 (p=0.016 vs. ctrl, n=8) respectively for 7 and 14 days of treatment (FIG. 3).

Figure 4:
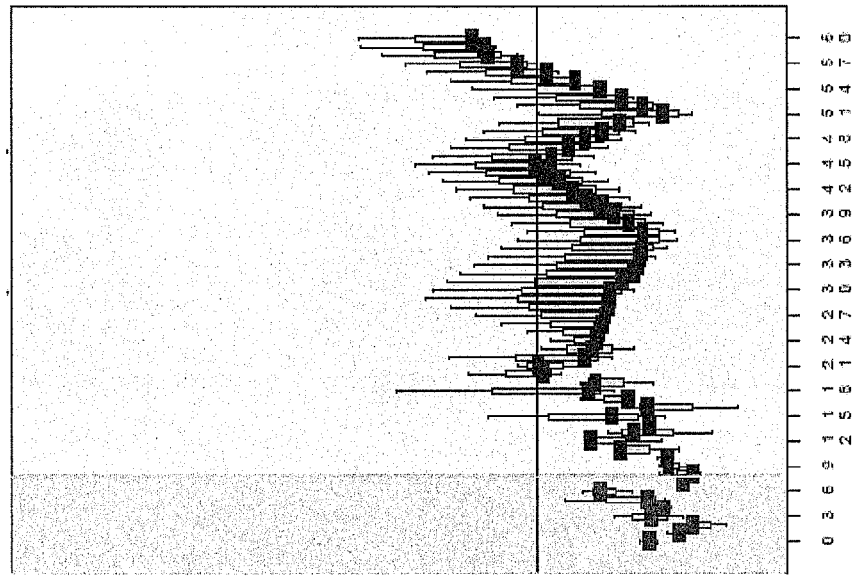
FIG. 4 shows the glycemia levels (mg/dl)) over time (days) in mice treated with (ML)-streptozotocin (STZ) at day 0 for 5 days, following administration from day +5 of Vehicle (Panel A) or Meraxin (15 mg/Kg) (Panel B) for 14 days.
Figure 4:
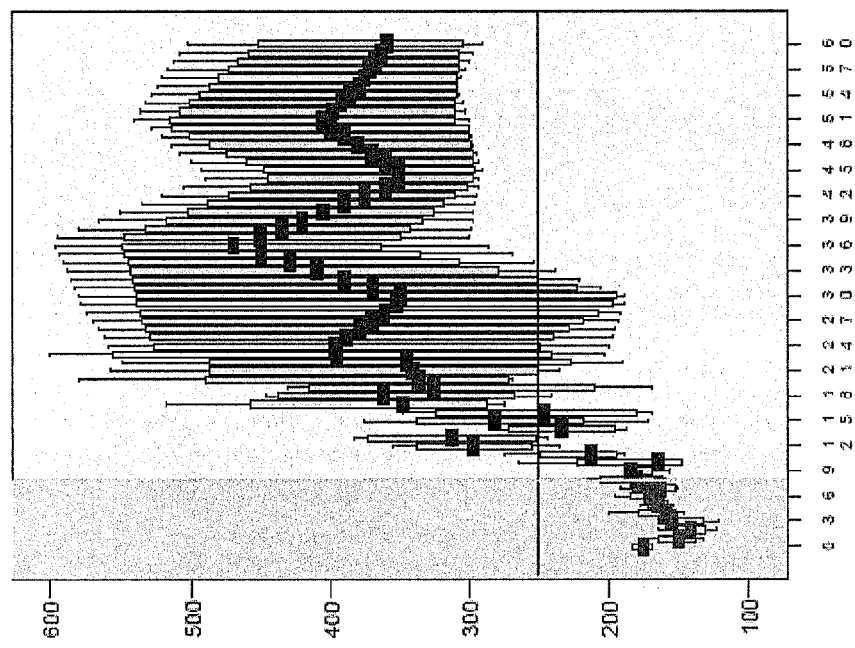

In a second set of experiments, the treatment with Meraxin for 14 days was started +5 (n=4) days after the first STZ injection to mimic the clinical setting of diabetes onset. As shown in FIG. 4, treatment with Meraxin up to day 19 clearly prevented diabetes onset. Furthermore, glycaemic levels remained constantly and significantly lower in Meraxin-treated mice compared to vehicle-treated mice for the whole 2-month observation period.

The invention claimed is:

1. A method of protecting pancreatic β-cells in an individual from structural and/or functional injury, the method comprising:

identifying an individual at risk for diabetes through obtaining a physical sample of a patient in need thereof; and administering to the patient a medicament comprising a compound of formula I, or a pharmaceutically acceptable salt thereof:

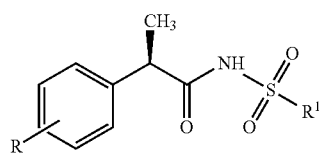

(I)

wherein $R^1$ is (C-$C_6$) alkyl and R is selected from the group consisting of linear or branched 4-($C_1$-$C_6$) alkyl, 4-trifluoromethane-sulfonyloxy, and 3-benzoyl.

2. The method of claim 1, wherein the medicament delays the onset and/or reduces the progression of diabetes in the individual.

3. The method of claim 1, wherein the medicament reduces the severity of diabetes following onset of diabetes in the individual.

4. The method of claim 1, wherein the medicament prevents the onset of diabetes in the individual.

5. The method of claim 1, wherein the compound of formula I is selected from the group consisting of R(-)-N-2-[(4-isobutylphenyl)propionyl]-methanesulfonamide and R(-)-2-[(4'-trifluoromethanesulfonyloxy)phenyl]propionyl-methanesulfonamide.

6. The method of claim 1, wherein the pharmaceutically acceptable salt is selected from the group consisting of lysine salts and sodium salts.

7. A method of delaying the onset and/or reducing the progression of diabetes in an individual, the method comprising:

identifying an individual at risk for diabetes; and administering to the individual a medicament comprising a compound of formula I, or a pharmaceutically acceptable salt thereof:

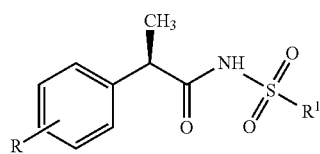

(I)

wherein R is selected from linear or branched 4-($C_1$-$C_6$) alkyl, 4-trifluoromethane-sulfonyloxy, and 3-benzoyl and $R^1$ is ($C_1$-$C_6$) alkyl.

8. The method of claim 7, wherein the medicament reduces the severity of diabetes following onset of diabetes in the individual.

9. The method of claim 7, wherein the medicament prevents the onset of diabetes in the individual.

10. The method of claim 7, wherein the compound of formula I is selected from the group consisting of R(-)-N-2-[(4-isobutylphenyl)propionyl]-methanesulfonamide and R(-)-2-[(4'-trifluoromethanesulfonyloxy)phenyl]propionyl-methanesulfonamide.

11. The method of claim 7, wherein the pharmaceutically acceptable salt is selected from the group consisting of lysine salts and sodium salts.

12. A method of inhibiting a diabetes-related rise in glycemic levels of an individual, the method comprising:

identifying an individual at risk for diabetes; and administering to the individual a medicament comprising a compound of formula I, or a pharmaceutically acceptable salt thereof:

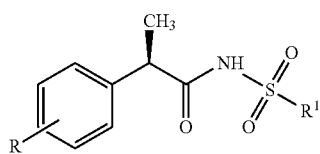

(I)

wherein R is selected from linear or branched 4-($C_1$-$C_6$) alkyl, 4-trifluoromethane-sulfonyloxy, and 3-benzoyl and $R^1$ is ($C_1$-$C_6$) alkyl.

13. The method of claim 12, wherein the medicament delays the onset and/or the progression of diabetes in the individual.

14. The method of claim 12, wherein the medicament reduces the severity of diabetes following onset of diabetes in the individual.

15. The method of claim 12, wherein the medicament prevents the onset of diabetes in the individual.

16. The method of claim 12, wherein the compound of formula I is selected from the group consisting of R(-)-N-2-[(4-isobutylphenyl)propionyl]-methanesulfonamide and R(-)-2-[(4'-trifluoromethanesulfonyloxy)phenyl]propionyl-methanesulfonamide.

17. The method of claim 12, wherein the pharmaceutically acceptable salt is selected from the group consisting of lysine salts and sodium salts.

* * * * *